United States Patent [19]

Agnès et al.

[11] 4,160,107

[45] Jul. 3, 1979

[54] PROCESS FOR THE PREPARATION OF ESTERS OF OXALIC ACID

[75] Inventors: Giovanni Agnès; Giuseppe Bimbi; Franco Guerrieri; Guglielmo Rucci, all of Novara, Italy

[73] Assignee: Montedison S.p.A., Milan, Italy

[21] Appl. No.: 941,400

[22] Filed: Sep. 11, 1978

Related U.S. Application Data

[63] Continuation of Ser. No. 783,047, Mar. 30, 1977, abandoned.

[30] Foreign Application Priority Data

Apr. 12, 1976 [IT]  Italy ............................. 22169 A/76

[51] Int. Cl.$^2$ ............................................. C07C 69/36
[52] U.S. Cl. .................................................. 560/204
[58] Field of Search ........................................ 560/204

[56] References Cited

U.S. PATENT DOCUMENTS

| | | | |
|---|---|---|---|
| 3,994,960 | 11/1976 | Yamazuki et al. | 560/204 |
| 4,005,128 | 1/1977 | Zehner | 560/204 |
| 4,005,129 | 1/1977 | Zehner | 560/204 |

FOREIGN PATENT DOCUMENTS 2213435  10/1973  Fed. Rep. of Germany ........... 560/204

*Primary Examiner*—Jane S. Myers
*Attorney, Agent, or Firm*—Morgan, Finnegan, Pine, Foley & Lee

[57] ABSTRACT

There is provided a process for the preparation of esters of oxalic acid comprising reacting at a temperature of between about 20° and 200° C. a copper (II) compound having the formula Cu(OR)X, where R is alkyl having from 1 to 8 carbon atoms and X is chlorine or bromine, with carbon monoxide in the presence of a catalyst selected from the group consisting of palladium salts, metallic palladium and zero valent palladium complexes.

12 Claims, No Drawings

PROCESS FOR THE PREPARATION OF ESTERS OF OXALIC ACID

CROSS-REFERENCE TO RELATED APPLICATIONS

This is a continuation of copending application Ser. No. 783,047, filed Mar. 30, 1977, now abandoned.

FIELD OF THE INVENTION

This invention relates to the preparation of oxalic acid esters. After preparation, the esters may be converted to the corresponding acids using conventional techniques, e.g., hydrolysis, and the like. Oxalic acid esters and oxalic acid are of considerable industrial interest. Oxalic acid is useful in the textile field as an auxiliary stripping agent in the dyeing of wool and as bleaching agents for natural fibers or as pickling agents for metal surfaces, and especially copper surfaces. Oxalic acid is also known in industry as a dehydrogenating agent for condensation reactions and the like. Esters of oxalic acid are useful as solvents, for example, as a solvent for the diethylester for cellulose.

BACKGROUND OF THE INVENTION

It is known to prepare oxalic esters by oxidative reaction of carbon monoxide and monobasic alcohols with oxygen and also with quinones, preferably in a substantially anhydrous medium, anhydrous for the presence of dehydrating substances, and catalyzed by Redox-systems in general consisting of the finely subdivided metal or of soluble salts or complexes (citrates, chelates) of a noble metal of the Pt group, such as, for instance, Pd, Os, and of a salt and/or a complex of another metal more electropositive than the previous ones, such as Fe, Co, Ni, Cu, Mn, etc., such as chlorides, acetates, etc., possessing several oxidative states.

The reaction is preferably conducted in the presence of co-catalysts and/or complexing agents consisting of soluble salts of alkaline metals (e.g., LiCl, KCl, etc.).

Nevertheless, processes of this type, because of the simultaneous occurrence of secondary reactions leading to the formation of carbonates, $CO_2$, esters-(acetates, formates, etc.), cannot be considered fully satisfactory from the industrial point of view owing to the low yields and because of the relatively burdensome operations involved, such as separation, purification, etc.

Moreover, the use of gaseous $CO+O_2$ mixtures with the corresponding risk of explosions constitutes a further serious obstacle to an industrial application.

On the other hand, the other processes of the prior art, for instance, by the dehydrogenation of sodium formate, subsequently converted to calcium oxalate, acidified, etc., or by oxidation of the propylene with $HNO_3$ catalyzed by Fe, Cr, etc., do not insure best results owing to the considerable technological and operational difficulties involved which make them little acceptable economically, especially for the mass production.

OBJECTS OF THE INVENTION

An object of this invention is that of providing a simple and economical process for the preparation of esters of oxalic acid that are free of the drawbacks of the art, and, in particular, securing high yields and purity of the products, representing a real progress over the technique of the art.

GENERAL DESCRIPTION OF THE INVENTION

This and still other objects, which will appear more clearly to the skilled in the art from the following description, are achieved according to this invention by a process for the preparation of esters of oxalic acid, characterized in that the oxalic acid esters are obtained by reacting a copper (II) compound of the formula Cu(OR)X wherein R represents an alkyl radical having from 1 to 8 carbon atoms, preferably an alkyl radical having from 1 to 4 carbon atoms; X represents a chlorine or bromine atom, preferably chlorine, with carbon monoxide in the presence of at least a palladium salt or a zero-valent palladium compound, possibly in a substantially anhydrous medium, at a temperature comprised between about 20° and 200° C.

The process may be schematically represented by the following equation:

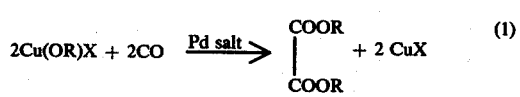

wherein R and X have the above given meaning.

The invention should be considered so much the more surprising, inasmuch as it represents a considerable overcoming of a prejudice existing in the technique of the prior art, which is quite explicit in teaching that copper compounds of the type used in this invention, by reaction with CO, in the absence of Pd and in similar parametric conditions, lead exclusively and quantitatively to the corresponding diester of the carbonic acid, according to the equation:

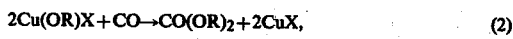

wherein R and X have the already given meaning; a prejudice that obviously would have dissuaded the expert in the art to undertake further research in that direction.

Oxalic esters are, at any rate, obtained by the reaction of carbon monoxide with the alkoxy-cupric Cu(OR)X salt, wherein R and X are as defined above, in the presence of a Pd-based catalyst, possibly in an inert solvent.

Catalysts that may be used in accordance with this invention are Pd salts soluble in the reaction medium or mixtures thereof such as halides, sulphates, nitrates, acetylacetonate, acetates, etc., preferably Pd (acetylacetonate)$_2$. It is also possible to use metal Pd or complexes of zero-valent Pd which are well known to the technician, such as Pd on carbon, or Pd complexes with binders such as phosphines, dibenzylideneacetone, etc.

The molar ratio of palladium with respect to the Cu(OR)X copper compound is preferably comprised between 0.0001 and 0.1 mols of Pd per 1 mol of the copper compound. Ratios different from these are acceptable but are not necessary.

The inert reaction medium preferably consists of monofunctional ROH alcohols, wherein R has the meaning already given, still preferably of methyl or ethyl alcohol, and/or of aliphatic or aromatic hydrocarbons that are inert at the reaction conditions, or mixtures thereof.

For purposes of illustration only, there have proved quite effective mixtures containing up to 75–95% of benzene and 25–5% of alcohol. Other inert solvents may be benzene, acetone, ethylacetate, tetrahydrofurane.

The carbon monoxide, which may be by itself or in the form of a synthetic gas combined with $H_2$, is fed at a partial pressure comprised between 1 and about 100 ata, and preferably between about 10 to 100 ata.

In the present specification, "atm" refers to atmospheres, and "ata" refers to absolute atmospheres.

The useful reaction temperature ranges from 20° to about 200° C., but preferably is comprised between 50° and about 120° C.

The reaction times may vary, depending on the temperature and the pressure employed, within wide intervals.

Whenever desired, the use of CO in admixture with inert gases is permissible.

The yields in ester according to reaction (1) of this process are practically quantitative with respect to the CO and the cupric compound, while Pd acts exclusively as the catalyst.

The separation of the reaction product from the solvent and from the catalyst may be easily achieved by distillation, etc., according to known techniques. From the ester the acid is easily obtainable by hydrolysis according to the conventional methods.

The distillation residue, containing the CuX salt and the catalyst, may be used for further reactions after the preliminary regeneration of the cupric Cu(OR)X compound, according to known methods, for instance, by oxidation with air and/or oxygen in an ROH alcoholic medium, wherein R and X are as defined above.

The Cu(OR)X compound may also be obtained according to another known method in the form of a complex with basic organic binders, such as, for instance, pyridine and picoline, and used as such without any difficulty in the process reaction.

Because of the milder operating conditions, the invention appears to be particularly convenient.

Other advantages consist in the selectivity for the desired products and in the reasonable reduction of the operational risks of explosivity, in the absence of $CO+O_2$ mixtures.

Finally, of particular interest is the possibility of using the mixtures of CO and hydrogen, as such, produced during the preparation of the synthesis gas, without thereby reducing the effectiveness of the process.

The invention will now be described in more detail by the following examples are set forth for illustrative purposes only and are not intended to be limiting.

SPECIFIC DESCRIPTION OF THE INVENTION

EXAMPLE 1

Into a stainless steel autoclave of 1 lt holding capacity, fitted with a glass vial, were loaded: 30 ml of methanol, 0.15 g of Pd(acetylacetonate)$_2$ and 3.06 g of Cu(OCH$_3$)Cl.

Thereupon there were loaded 100 atm. of CO, and the temperature was brought up to 45° C. The reaction mass was then kept over 6 hours under stirring at the same temperature of 45° C. The raw reaction mass was then distilled, and there were obtained 1.39 grams of methyl oxalate having a boiling point of 65°–67° C./12 mmHg and a melting point of 53° C. The yield reckoned on the reacted Cu(OCH$_3$)Cl turned out to be 100%.

EXAMPLE 2

Proceeding in the same way as in Example 1, into the autoclave were loaded: 25 ml of benzene, 5 ml of methanol, 3.43 grams of Cu(OCH$_3$)Cl, and 0.15 g of Pd(acetylacetonate)$_2$. Under the same operational conditions as in Example 1 there were obtained 1.56 grams of methyl oxalate. Yield reckoned on the reacted Cu(OCH$_3$)Cl was 100%.

EXAMPLE 3

Proceeding as in Example 1, into the autoclave were loaded: 30 ml of methanol, 0.15 g of Pd(acetylacetonate)$_2$, 3.15 g of Cu(OCH$_3$)Cl. Then there were fed 100 atm. of CO; thereafter the autoclave was left for over 5 hours at room temperature. Thereby were obtained 1.43 g of methyl oxalate. The yield on the reacted Cu(OCH$_3$)Cl amounted to 100%.

EXAMPLE 4

Proceeding as in Example 1, into the autoclave were loaded: 30 ml of methanol, 0.15 g of Pd(acetylacetonate)$_2$, and 2.91 g of Cu(OCH$_3$)Cl. Thereupon there were fed 100 atm. of CO, and the autoclave was left at room temperature for over 4 hours. Thereby were obtained 1.08 g of methyl oxalate. The yield on the reacted Cu(OCH$_3$)Cl was 82%.

EXAMPLE 5

Proceeding as in Example 1, into the autoclave were loaded: 30 ml of methanol, 0.15 g of Pd(acetylacetonate)$_2$, and 3.12 g of Cu(OCH$_3$)Cl. Thereupon into the autoclave were fed 12 atm. of CO and the autoclave was then left at room temperature for over 11 hours. Thereby were obtained 1.41 grams of methyl oxalate. The yield on the reacted Cu(OCH$_3$)Cl was 100%.

EXAMPLE 6

Proceeding as in Example 1, into the autoclave were loaded: 3 ml of methanol, 30 ml of $C_6H_6$, 0.15 g of Pd(acetylacetonate)$_2$ and 2.88 g of Cu(OCH$_3$)Cl. Thereupon there were fed 50 atm. of CO and 50 atm. of $H_2$, then bringing the temperature up to 45° C. The autoclave was then left at this temperature for over 6 hours. There were obtained 1.10 g of methyl oxalate. The yield calculated on the reacted Cu(OCH$_3$)Cl proved to be 85%.

EXAMPLE 7

Proceeding according to Example 1, the autoclave was loaded with: 2 ml of methanol, 30 ml of benzene, 0.15 g of Pd(acetylacetonate)$_2$, and 3.28 g of Cu(OCH$_3$)Cl. Thereupon into the autoclave were fed 50 atm. of CO and 50 atm. of $H_2$ and then the whole was brought up to a temperature of 60° C. The autoclave was then left at this temperature for over 2 hours. Thereby were obtained 1.488 g of methyl oxalate. The yield, calculated on the reacted Cu(OCH$_3$)Cl was 100%.

EXAMPLE 8

Proceeding as in Example 1, the autoclave was loaded with: 30 ml of benzene, 0.15 g of Pd(acetylacetonate)$_2$ and 2.88 g of Cu(OCH$_3$)Cl. Thereupon into the autoclave were fed 50 atm. of CO and the temperature was brought up to 45° C. Then the autoclave was left at this temperature for over 6 hours. Thereby were obtained 0.466 grams of methyl oxalate.

EXAMPLE 9

It was proceeded as in Example 8, except that the temperature in the autoclave was 70° C. There were obtained 1.174 g of methyl oxalate.

EXAMPLE 10

It was proceeded as in Example 8, except that the reaction time was 2 hours. Thereby were obtained 1.020 g of methyl oxalate.

EXAMPLE 11

It was proceeded in the same way as in Example 8, except that instead of benzene there was used acetone. There were obtained 0.646 g of methyl oxalate.

EXAMPLE 12

It was proceeded as in Example 8, except that instead of benzene there was used ethylacetate. There were obtained 0.656 g of methyl oxalate.

EXAMPLE 13

It was proceeded as in Example 8, except that instead of benzene there was used tetrahydrofurane. Thereby were obtained 0.692 grams of methyl oxalate.

EXAMPLE 14

Proceeding as in Example 1, into the autoclave were loaded: 30 ml of benzene, 2 ml of methanol, 0.15 g of Pd(acetylacetonate)$_2$ and 2.94 g of Cu(OCH$_3$)Cl. Into the autoclave were then loaded 50 atm. of CO and the temperature was brought up to 60° C. The autoclave was then left at this temperature for over 2 hours. Thereby were obtained 1.390 g of methyl oxalate. The yield on the reacted Cu(OCH$_3$)Cl was 100%.

EXAMPLE 15

Proceeding as in Example 1, but in the absence of solvents, into the autoclave were loaded: 0.60 g of Pd(acetylacetonate)$_2$, 2.3 g of Cu(OCH$_3$)Cl. The autoclave was then loaded with 100 atm. of CO and the temperature was brought up to 60° C. The autoclave was then left at this temperature for over 6 hours. There were obtained 0.330 grams of methyl oxalate.

EXAMPLE 16
(comparison example in the absence of catalysis)

Proceeding as in Example 1, the autoclave was loaded with: 40 ml of methanol, 2.88 g of Cu(OCH$_3$)Cl. Thereupon there were fed in 100 atm. of CO and the temperature was brought up to 50° C. It is then left at this temperature for 4 hours. No trace of oxalate could be found.

EXAMPLE 17

3.8 g of Cu(OCH$_3$)Br were prepared "in situ" from CuBr$_2$ (5 grams) and CH$_3$ONa (1.2 grams) in 30 ml of methanol. 0.15 g of Pd(acetylacetonate)$_2$ were then added. The autoclave was then pressurized with CO at 50 atm. and was maintained at 45° C. for over 6 hours, under stirring. Thereby were obtained 0.558 grams of methyl oxalate.

EXAMPLE 18

Proceeding as in Example 1, into the autoclave were loaded: 2.9 g of Cu(OCH$_3$)Cl, 30 ml of benzene, 2 ml of methanol, and 0.15 g of Pd(acetylacetonate)$_2$ and this mixture was then maintained under stirring at 60° C. for over 3 hours and under a pressure of 5 atm. of CO. Thereby were obtained 0.93 g of methyl oxalate.

EXAMPLE 19

Into a glass flask, fitted with a magnetic stirrer, were loaded 2.9 g of Cu(OCH$_3$)Cl, 20 ml of benzene, 10 ml of methanol and 0.15 g of Pd(acetylacetonate)$_2$. The flask was then degassed with a flow of CO and put into communication with a CO loaded buret. Stirring was then kept on for over 10 hours maintaining the reaction mixture at a temperature comprised between 50° and 60° C. Thereby were obtained 0.54 grams of methyl oxalate.

EXAMPLE 20

3.82 g of Cu(OC$_4$H$_9$)Cl were prepared "in situ" from 3 g of CuCl$_2$ and 2.1 g of C$_4$H$_9$ONa in 50 ml of butanol. The mass was then diluted with 30 ml of benzene and 0.15 grams of Pd(acetylacetonate)$_2$ were added, whereupon one proceeded as in Example 1, under a pressure of 50 atm. of CO for over 3 hours at 60° C. There were thus obtained 1.65 g of butyl oxalate.

We claim:

1. Process for the preparation of esters of oxalic acid having the formula ROOC—COOR by oxidative reaction in the presence of palladium-based catalysts, characterized in that the oxalic esters are obtained by the reaction of a copper (II) compound having the formula Cu(OR)X, wherein R represents a radical selected from among alkyls having from 1 to 8 carbon atoms, and X is chosen from between chlorine and bromine atom, with carbon monoxide in the presence of a catalyst selected from the group consisting of Pd salts, metal Pd and zero valent Pd complexes, at a temperature of between 20° and about 200° C., in the absence of O$_2$.

2. Process according to claim 1, characterized in that the catalyst consists of a Pd containing component selected from the group consisting of Pd halides, Pd nitrate, Pd acetate, Pd sulphate and Pd acetylacetonate, Pd on carbon and Pd complexes with phosphines and/or with dibenzylidene-acetone.

3. Process according to claim 1, characterized in that the catalyst consists of Pd acetylacetonate.

4. Process according to claim 1, characterized in that the copper (II) compound is Cu(OR)X, wherein R is a radical selected from the group consisting of alkyls having from 1 to 4 carbon atoms and X is either a chlorine or a bromine atom.

5. Process according to claim 1, characterized in that the reaction is conducted in a substantially anhydrous medium selected from the group consisting of monofunctional alcohols of formula ROH, wherein R is an alkyl having from 1 to 4 carbon atoms, benzene, acetone, ethylacetate, tetrahydrofurane and/or mixtures thereof.

6. Process according to claim 5, characterized in that an anhydrous medium is selected from the group consisting of methyl alcohol and ethyl alcohol.

7. Process according to claim 1, characterized in that the molar ratio of Pd with respect to the copper compound Cu(OR)X is comprised between 0.0001 and 0.1 mol of Pd per 1 mol of copper compound.

8. Process according to claim 1, characterized in that the reaction is conducted between about 50° and 120° C.

9. Process according to claim 1, characterized in that the reaction is conducted under partial CO pressures comprised between about 10 and 100 ata.

10. Process according to claim 1, characterized in that the carbon monoxide is fed in admixture with gases inert under reaction conditions.

11. Process according to claim 10 wherein the carbon monoxide is fed in admixture with H$_2$ coming from the industrial preparation of the synthesis gas.

12. Process according to claim 4 wherein R is methyl and X is chlorine.

* * * * *